(12) United States Patent
Harper

(10) Patent No.: US 8,730,058 B2
(45) Date of Patent: *May 20, 2014

(54) ANALYTE MONITORING SYSTEM HAVING AN ALERT

(71) Applicant: Abbott Diabetes Care Inc., Alameda, CA (US)

(72) Inventor: Wesley Scott Harper, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,356

(22) Filed: Jul. 29, 2013

(65) Prior Publication Data

US 2013/0314250 A1    Nov. 28, 2013

Related U.S. Application Data

(63) Continuation of application No. 12/761,387, filed on Apr. 15, 2010, now Pat. No. 8,497,777.

(60) Provisional application No. 61/169,654, filed on Apr. 15, 2009, provisional application No. 61/169,652, filed on Apr. 15, 2009.

(51) Int. Cl.
*G08B 21/00* (2006.01)

(52) U.S. Cl.
USPC ............ 340/870.16; 340/573.1; 600/301; 600/347

(58) Field of Classification Search
USPC .......... 340/870.16, 573.1, 539.1; 436/95; 600/301, 316, 347, 365
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |

(Continued)

FOREIGN PATENT DOCUMENTS

| | | |
|---|---|---|
| CA | 2468577 | 6/2003 |
| CA | 2678336 | 5/2008 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — John A Tweel, Jr.
(74) *Attorney, Agent, or Firm* — Jackson & Co., LLP

(57) ABSTRACT

Described herein are analyte monitoring systems including a receiver or data processing component that is configured to automatically issue a first alert notification when a first predetermined number of consecutive data packets are not received from the sensor/sensor electronics, and automatically issue a second alert notification when a second predetermined number of consecutive data packets are not received by the sensor/sensor electronics. The receiver may also be configured to enable a user to disenable alert or alarm notifications that are triggered based on detected events.

20 Claims, 5 Drawing Sheets

(56) References Cited

U.S. PATENT DOCUMENTS

| | | |
|---|---|---|
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,202,261 A | 4/1993 | Musho et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,328,460 A | 7/1994 | Lord et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |

(56) References Cited

U.S. PATENT DOCUMENTS

| | | |
|---|---|---|
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,025,425 B2 | 4/2006 | Kovatchev et al. |
| 7,029,444 B2 | 4/2006 | Shin et al. |
| 7,041,068 B2 | 5/2006 | Freeman et al. |
| 7,043,287 B1 | 5/2006 | Khalil et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 | 12/2006 | Vachon |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,241,266 B2 | 7/2007 | Zhou et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,401,111 B1 | 7/2008 | Batman et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,774,145 B2 | 8/2010 | Brauker et al. |
| 7,778,680 B2 | 8/2010 | Goode, Jr. et al. |
| 7,826,981 B2 | 11/2010 | Goode et al. |
| 7,885,698 B2 | 2/2011 | Feldman |
| 7,899,511 B2 | 3/2011 | Shults et al. |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,928,850 B2 | 4/2011 | Hayter et al. |
| 7,974,672 B2 | 7/2011 | Shults et al. |
| 7,976,467 B2 | 7/2011 | Young et al. |
| 8,010,174 B2 | 8/2011 | Goode et al. |
| 8,066,639 B2 | 11/2011 | Nelson et al. |
| 8,216,138 B1 | 7/2012 | McGarraugh et al. |
| 8,497,777 B2 * | 7/2013 | Harper .................. 340/573.1 |
| 2002/0019022 A1 | 2/2002 | Dunn et al. |
| 2002/0042090 A1 | 4/2002 | Heller et al. |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |

(56) References Cited

U.S. PATENT DOCUMENTS

| | | |
|---|---|---|
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0267300 A1 | 12/2004 | Mace |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0229512 A1 | 10/2006 | Petisce et al. |
| 2006/0247508 A1 | 11/2006 | Fennell |
| 2006/0253296 A1 | 11/2006 | Liisberg et al. |
| 2006/0264785 A1 | 11/2006 | Dring et al. |
| 2006/0272652 A1 | 12/2006 | Stocker et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038053 A1 | 2/2007 | Berner et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0093786 A1 | 4/2007 | Goldsmith et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0197889 A1 | 8/2007 | Brauker et al. |
| 2007/0203407 A1 | 8/2007 | Hoss et al. |
| 2007/0203966 A1 | 8/2007 | Brauker et al. |

(56) References Cited

U.S. PATENT DOCUMENTS

| | | |
|---|---|---|
| 2007/0213657 A1 | 9/2007 | Jennewine et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0270672 A1 | 11/2007 | Hayter et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234992 A1 | 9/2008 | Ray et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saudara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0278331 A1 | 11/2008 | Hayter et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319279 A1 | 12/2008 | Ramsay et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054750 A1 | 2/2009 | Jennewine |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0099436 A1 | 4/2009 | Brister et al. |
| 2009/0105570 A1 | 4/2009 | Sloan et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |

(56) References Cited

U.S. PATENT DOCUMENTS

| | | |
|---|---|---|
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0191085 A1 | 7/2010 | Budiman |
| 2010/0191087 A1 | 7/2010 | Talbot et al. |
| 2010/0191472 A1 | 7/2010 | Doniger et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0214104 A1 | 8/2010 | Goode et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0240976 A1 | 9/2010 | Goode et al. |
| 2010/0259543 A1 | 10/2010 | Tarassenko et al. |
| 2010/0261987 A1 | 10/2010 | Kamath et al. |
| 2010/0265073 A1 | 10/2010 | Harper |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324403 A1 | 12/2010 | Brister et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0077469 A1 | 3/2011 | Blocker et al. |
| 2011/0077490 A1 | 3/2011 | Simpson et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0178378 A1 | 7/2011 | Brister et al. |
| 2011/0184752 A1 | 7/2011 | Ray et al. |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2012/0035445 A1 | 2/2012 | Boock et al. |
| 2012/0040101 A1 | 2/2012 | Tapsak et al. |

(56) References Cited

U.S. PATENT DOCUMENTS

| | | |
|---|---|---|
| 2012/0046534 A1 | 2/2012 | Simpson et al. |
| 2012/0078071 A1 | 3/2012 | Bohm et al. |
| 2012/0108934 A1 | 5/2012 | Valdes et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2031534 | 3/2009 |
| EP | 1725163 | 12/2010 |
| WO | WO-96/25089 | 8/1996 |
| WO | WO-96/35370 | 11/1996 |
| WO | WO-98/35053 | 8/1998 |
| WO | WO-99/27849 | 6/1999 |
| WO | WO-99/28736 | 6/1999 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/057027 | 7/2003 |
| WO | WO-03/076893 | 9/2003 |
| WO | WO-03/082091 | 10/2003 |
| WO | WO-03/085372 | 10/2003 |
| WO | WO-2004/060455 | 7/2004 |
| WO | WO-2004/061420 | 7/2004 |
| WO | WO-2005/041766 | 5/2005 |
| WO | WO-2005/057175 | 6/2005 |
| WO | WO-2005/065538 | 7/2005 |
| WO | WO-2005/065542 | 7/2005 |
| WO | WO-2005/089103 | 9/2005 |
| WO | WO-2006/020212 | 2/2006 |
| WO | WO-2006/024671 | 3/2006 |
| WO | WO-2006/072035 | 7/2006 |
| WO | WO-2006/079114 | 7/2006 |
| WO | WO-2006/118947 | 11/2006 |
| WO | WO-2007/016399 | 2/2007 |
| WO | WO-2007/019289 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/048452 | 4/2008 |
| WO | WO-2008/052374 | 5/2008 |
| WO | WO-2008/062099 | 5/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/144445 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/062898 | 6/2010 |
| WO | WO-2011/000528 | 1/2011 |
| WO | WO-2011/104616 | 9/2011 |

OTHER PUBLICATIONS

Bennion, N., et al., "Alternate Site Glucose Testing: A Crossover Design", *Diabetes Technology & Therapeutics*, vol. 4 No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56 No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

(56) References Cited

OTHER PUBLICATIONS

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2010/031322, International Search Report and Written Opinion of the International Searching Authority mailed Jun. 16, 2010.

PCT Application No. PCT/US2010/031322, International Preliminary Report on Patentability and Written Opinion of the International Searching Authority mailed Oct. 27, 2011.

U.S. Appl. No. 12/761,387, Notice of Allowance mailed May 6, 2013.

U.S. Appl. No. 12/761,387, Office Action mailed Aug. 30, 2012.

\* cited by examiner

ANALYTE MONITORING SYSTEM HAVING AN ALERT

RELATED APPLICATIONS

The present application is a continuation of U.S. patent application Ser. No. 12/761,387 filed Apr. 15, 2010, now U.S. Pat. No. 8,497,777, which claims priority under 35 U.S.C. §119(e) to U.S. Provisional Patent Application No. 61/169,654, entitled "Analyte Monitoring System with Alert for Missed Data packet", filed on Apr. 15, 2009 and U.S. Provisional Patent Application No. 61/169,652, entitled "Analyte Monitoring System with Muted Alarm Capability", filed on Apr. 15, 2009, the disclosures of each of which are incorporated herein by reference in their entirety for all purposes.

BACKGROUND

Diabetes Mellitus is an incurable chronic disease in which the body does not produce or properly utilize insulin. Insulin is a hormone produced by the pancreas that regulates blood glucose. In particular, when blood glucose levels rise, e.g., after a meal, insulin lowers the blood glucose levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

People suffering from diabetes often experience long-term complications. Some of these complications include blindness, kidney failure, and nerve damage. Additionally, diabetes is a factor in accelerating cardiovascular diseases such as atherosclerosis (hardening of the arteries), which often leads to stroke, coronary heart disease, and other diseases, which can be life threatening.

The severity of the complications caused by both persistent high glucose levels and blood glucose level fluctuations has provided the impetus to develop diabetes management systems and treatment plans. In this regard, diabetes management plans historically included multiple daily testing of blood glucose levels typically by a finger-stick to draw and test blood. The disadvantage with finger-stick management of diabetes is that the user becomes aware of his blood glucose level only when he performs the finger-stick. Thus, blood glucose trends and blood glucose snapshots over a period of time is unknowable.

More recently, diabetes management has included the implementation of glucose monitoring systems. Glucose monitoring systems have the capability to continuously monitor a user's blood glucose levels. Thus, such systems have the ability to illustrate not only present blood glucose levels but a snapshot of blood glucose levels and blood glucose fluctuations over a period of time. Further, when monitoring the blood glucose levels, the glucose monitoring systems have the capability to output an alert notification to notify the user of an event, such as a hyperglycemic or hypoglycemic event. Although the alert features are a big advantage to managing diabetes, sometimes an alert, such as the loud sounding of an audible alarm, can occur at an inopportune time.

Additionally, the accuracy of continuous glucose monitoring systems depend on the proper and prompt relay of data information about minute to minute glucose levels from a sensor to a receiver component of the system. When the data information fails to reach the receiver, the lack of glucose data can not only affect the displayed glucose readings to the user, but also provide the user with a false sense of security.

Therefore, a need exists for a user to have the capability to selectively disenable and re-enable alert notification features of a glucose monitoring system for a predetermined period of time and for the analyte monitoring system to sound an alarm or otherwise alert the user to missed data packets so that the user can intervene.

SUMMARY

Embodiments of the present disclosure include analyte monitoring systems including a receiver or data processing component configured to automatically issue a first alert notification when a first predetermined number of consecutive data packets are not received from the sensor/sensor electronics, and automatically issue a second alert notification when a second predetermined number of consecutive data packets are not received by the sensor/sensor electronics. The receiver may be configured to enable a user to disenable alert or alarm notifications that are triggered based on detected events.

In certain embodiments, the receiver has the capability of displaying blood glucose readings related to the received data. The receiver is also configured to output an alert notification based on an event, such as, for example, a hypoglycemic event, a hyperglycemic event, an impending hypoglycemic event, an impending hyperglycemic event, or when a predetermined number of consecutive data packets are not received by the receiver. Additionally, the receiver is configured to provide a user the capability to selectively disenable the alarm for a predetermined time period and also re-enable the alarm prior to elapse of the predetermined time period.

In certain embodiments, the alert can be a visual alert, such as a displayed icon, an audible alert, such as a beep or music, a tactile alert such as a vibration of a system component or a combination thereof. The alert can have multiple modes of notification. In one embodiment, the alert is tri-modal. Thus, the alert can simultaneously include an audible, visual, and tactile notification. In this regard, the receiver can be configured to mute only one or two of the three alarm modes. For the purpose of illustration and not limitation, the audible notification can be muted by the user while the tactile (e.g., vibration) and visual (e.g., icon) notifications are not disenabled. Thus, when an event triggers the alert notification, the user is notified of the event or condition by feeling the vibration and/or seeing the icon.

As explained in greater detail below, the alert notification, or components thereof, can be selectively disenabled for a predetermined amount of time up to a maximum predetermined period of time, such as, for example, twelve hours. In this regard, the receiver can be configured to allow the user to select disenabling the alarm for an entire predetermined period (e.g., two hours, six hours) or alternatively, the selective disenablement of the alarm for the predetermined period can be set in one-hour increments or less.

Embodiments further include a receiver that may be configured such that the alert is incapable of being disenabled for a critical event such as a low glucose level, a decreasing blood glucose trend, a hypoglycemic event, or a blood glucose level above or below a particular threshold level. In this regard, the receiver is capable of allowing a user to disenable the alarm only for non-critical events, such as but not limited to, battery status, sensor life, and the like.

INCORPORATION BY REFERENCE

The following patents, applications and/or publications are incorporated herein by reference for all purposes: U.S. Pat.

Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 12/131,012; 12/242,823; 12/363,712; 12/495,709; 12/698,124; 12/699,653; 12/699,844; and 12/714,439 and U.S. Provisional Application Nos. 61/230,686 and 61/227,967.

DETAILED DESCRIPTION

Figure 1:
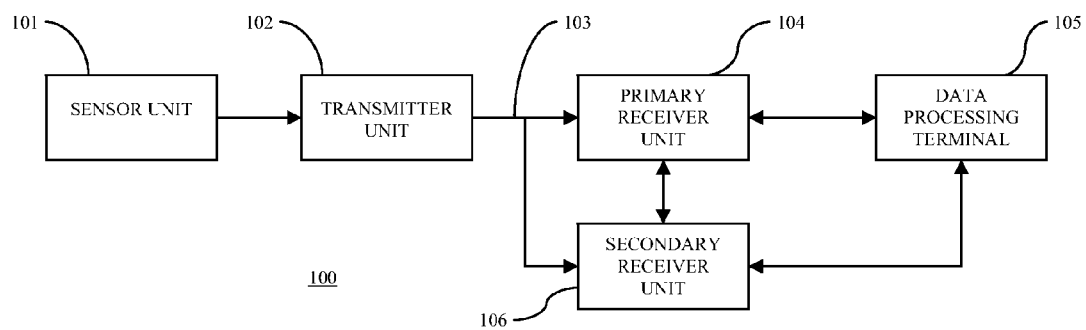
FIG. 1 illustrates a block diagram of an analyte monitoring system for practicing one or more embodiments of the present disclosure.

Reference will now be made in detail to the embodiments of the present disclosure, examples of which are illustrated in the accompanying figures. As such, various aspects will be described in conjunction with the detailed description of the device. However, there is no intent to limit the scope of the present disclosure to the specific embodiments described herein.

Generally, the present disclosure is directed to an analyte monitoring system comprising a sensor operatively in contact with an analyte to be monitored, a transmitter operatively coupled to the sensor and a receiver for receiving data information from the transmitter relating to the concentration or amount of the analyte. The transmitter, which is operatively coupled to the sensor receives the raw data signals and processes the signals into a data packet. Each data packet comprises three values, the current analyte value and the two immediately preceding analyte values. The data packet is transmitted to a receiver component, which is configured to issue an alert when at least two consecutive data packets are missed or otherwise not received from the transmitter.

The receiver includes a display unit for displaying the analyte amount or concentration (e.g., mg/dL) to a user. In this regard, the term "user" includes but is not limited to the actual subject being monitored. For example, it is contemplated that the "user" could be a caretaker for the monitored subject. The analyte monitoring system is capable of continuously or intermittently monitoring an analyte in a biological fluid. In this regard, the biological fluid can be blood, interstitial fluid, urine or another fluid containing the analyte to be monitored.

The analyte monitoring system is configured to provide a user the capability to selectively disenable an alarm notification of the occurrence of an event for a predetermined period of time and selectively re-enable the alarm prior to elapse of the predetermined period of time. In certain embodiments, the event which triggers an alarm output notification can include, for example, analyte events, data loss events and system events.

In one embodiment, the analyte monitoring system is a continuous glucose monitoring system. In this regard, the analyte events are glucose events and include but are not limited to low glucose levels (e.g., when single or continuous glucose level is below a threshold), high glucose levels (e.g, when a single or continuous glucose level is above a threshold), decreasing glucose trend or increasing glucose trend. For the purpose of illustration, there are multiple ways to configure an analyte monitoring system to output an alarm notification based on an increasing or decreasing glucose trend. For example, the trend information can be based on multiple glucose datapoints in which the rate of change indicates a trend, or alternatively, a projected trend information can be based on predicting or projecting that the glucose level will exceed a particular threshold value based on a current trend.

Data loss events include but are not limited to a disconnection between the receiver and transmitter, improper insertion or implantation of the sensor, expired calibration, sensor error (e.g., not being able to calculate glucose), transmitter error (e.g., high work current noise, persistent skin temperature out of range, etc), or receiver error (e.g., RF data packet timing synchronization between CGE and UI processor was lost). System events include but are not limited to battery status (e.g., one week of battery remains, replacement battery needed), failed calibration, calibration request, early signal attenuation, acceleration of most recent valid data is too large, high signal saturation detected by transmitter, sensitivity is too high or too low, outlier detected, lost preferences, RF connection has been down for a predetermined time period (e.g., five minutes), 10 g data corrupted, detected insertion transient, and sensor removal.

FIG. 1 illustrates an analyte monitoring system 100 of the present disclosure. As shown in FIG. 1, the analyte monitoring system 100 includes sensor 101 operatively coupled to a transmitter unit 102. The transmitter unit is in operative communication with a primary receiver 104 via communication path 103. In certain embodiments, the analyte monitoring system can further include a secondary receiver 106. In certain embodiments, each of the receivers 104, 106 may be configured to transmit data information to a remote processor 105.

In certain embodiments, the sensor 101 of the analyte monitoring system 100 includes a substrate, a working electrode, a counter electrode, and a reference electrode. The working electrode, the counter electrode and the reference electrode are formed from conductive material. Examples include, but are not limited to, gold, carbon, Ag/Cl, and the like. In one embodiment, the substrate and electrodes are arranged in a stacked orientation, such as when insulating material is disposed between the electrodes.

A sensing layer, which includes at least one immobilized enzyme and an immobilized mediator agent is disposed on at least a portion of at least the working electrode. In one embodiment, the immobilized molecule is glucose oxidase and the mediator agent includes a noble metal, such as but not limited to osmium. The sensor can further include a biocompatible layer. The biocompatible layer is disposed on at least a portion of the sensing layer. In one embodiment, the biocompatible membrane and the sensing layer are partially bonded to define a heterogeneous multilayer.

In certain embodiments, the sensor 101 is in operative contact with an analyte. The term "analyte" refers to a substance or chemical constituent in a biological fluid, such as for example, blood or interstitial fluid. For example and not limitation, the analyte can be glucose, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, peroxide, prostate-specific antigen, prothrombin, RNA, thyroid stimulating hormone, and troponin. However, other analytes can be monitored as would be understood by one of ordinary skill in the art.

In some embodiments, sensor 101 is implantable into a subject's body for a period of time (e.g., three to five days) to contact and monitor an analyte present in a biological fluid. In this regard, the sensor can be disposed in a subject at a variety of sites, including intramuscularly, transcutaneously, intravascularly, or in a body cavity. Sensor 101 is configured to generate data signals relative to the amount or concentration of the analyte to be monitored.

Sensor 101 operatively contacts the analyte to be measured and generates raw data signals relating to the amount or concentration of the analyte detected. In certain embodiments, transmitter 102 is operatively coupled to sensor 101 and obtains information relating to the data signals from sensor 101. The transmitter 102 processes the data signals (e.g., encodes signals) received from the sensor 101 into a data packet. The data packet comprises a current analyte value and the two immediately preceding analyte values. The data packets are transmitted to receiver 104 via radiofrequency communications link 103.

In one embodiment, the transmitter 102 also includes a temperature sensor. In this regard, the temperature sensor measures an ambient temperature of the system. Alternatively, the transmitter can be configured to be worn on the skin of a user. Thus, the temperature sensor measures the skin temperature of the user.

The analyte monitoring system 100 also includes a receiver 104, which accepts analyte values from the transmitter over a communication link 103. Communication link 103 may be a wired communication link or a wireless communication link utilizing protocols including, but not limited to, radio frequency (RF), radio frequency identification (RFID), infrared (IR) or Bluetooth® communication protocols. In certain embodiments, the receiver 104 comprises an input device for receiving user input, a processor, and a computer readable medium for storing data relating to the operation of the analyte monitoring device and software, which when executed by the processor, determines whether an alert condition exists, whether the alert is disenabled or whether a data packet from the transmitter is not received or otherwise missed by the receiver. Thus, the receiver is configured to expect a data packet and issue an alert when an expected data packet is not received. Furthermore, the receiver may also include a memory that is capable of logging analyte concentration or analyte amount values. The receiver 104 may also allow a user to erase the logged analyte concentration or amount values.

As will be discussed in further detail below, the receiver 104 is configured to expect a data packet from the transmitter 102 at predetermined time intervals, such as, for example, every five minutes or less. In another embodiment, the receiver 104 is configured to expect a data packet from the transmitter 102 every minute or less. Still yet other embodiments provide that the user may select how often the receiver 104 should expect a data packet from the transmitter 102. Additionally, it is contemplated that data packets may be expected by the receiver 104 at different times depending on a condition of the user. For example, when a critical event or semi-critical event is detected, the receiver 104 may expect data packets more frequently than when continuous glucose readings are more stable.

In certain embodiments, the receiver 104 alerts the user to reconnect the receiver or the transmitter if a predetermined number of consecutive data packets are not received by the receiver 104. For example, if three consecutive data packets are not received by the receiver, an alert is issued. The alert can be an auditory alert, a visual alert, a tactile alert, or a combination thereof. Still yet other embodiments provide that the alert can be a continuous alert if the receiver fails to receive more than five consecutive data packets from the transmitter. The analyte monitoring system can be configured to automatically disengage an alert notifying a user of non-receipt of data packets upon the subsequent receipt of a data packet.

The receiver 104 uses the data to compute an analyte concentration or amount. The receiver 104 can be configured to display glucose values. In one embodiment, the receiver 104 includes two interconnected central processors. In one embodiment, one central processor is configured for displaying images on a display screen such as an LCD screen, user input and output functionality, as well as handling the user-interface of the receiver 104. The second central processor may be configured for test strip measurements, such as calibration, radiofrequency link radio interface, and a real time clock.

As discussed above, the receiver 104 also includes a display for displaying an indication of the level of the measured analyte as well as notifications of alerts. In one embodiment, the display unit may be separate from the receiver. In the alternative, the display unit can be coupled to the receiver. In some embodiments, the receiver and/or display unit may include a variety of components, such as, for example, a transmitter, an analyzer, a data storage unit, a watchdog circuit, an input device, a power supply, a clock, a lamp, a pager, a telephone interface, a computer interface, an alarm or alarm system, a radio, and a calibration unit. In some embodiments, the receiver 104 provides a display screen for a line graph that plots logged analyte values versus time.

Figure 2:
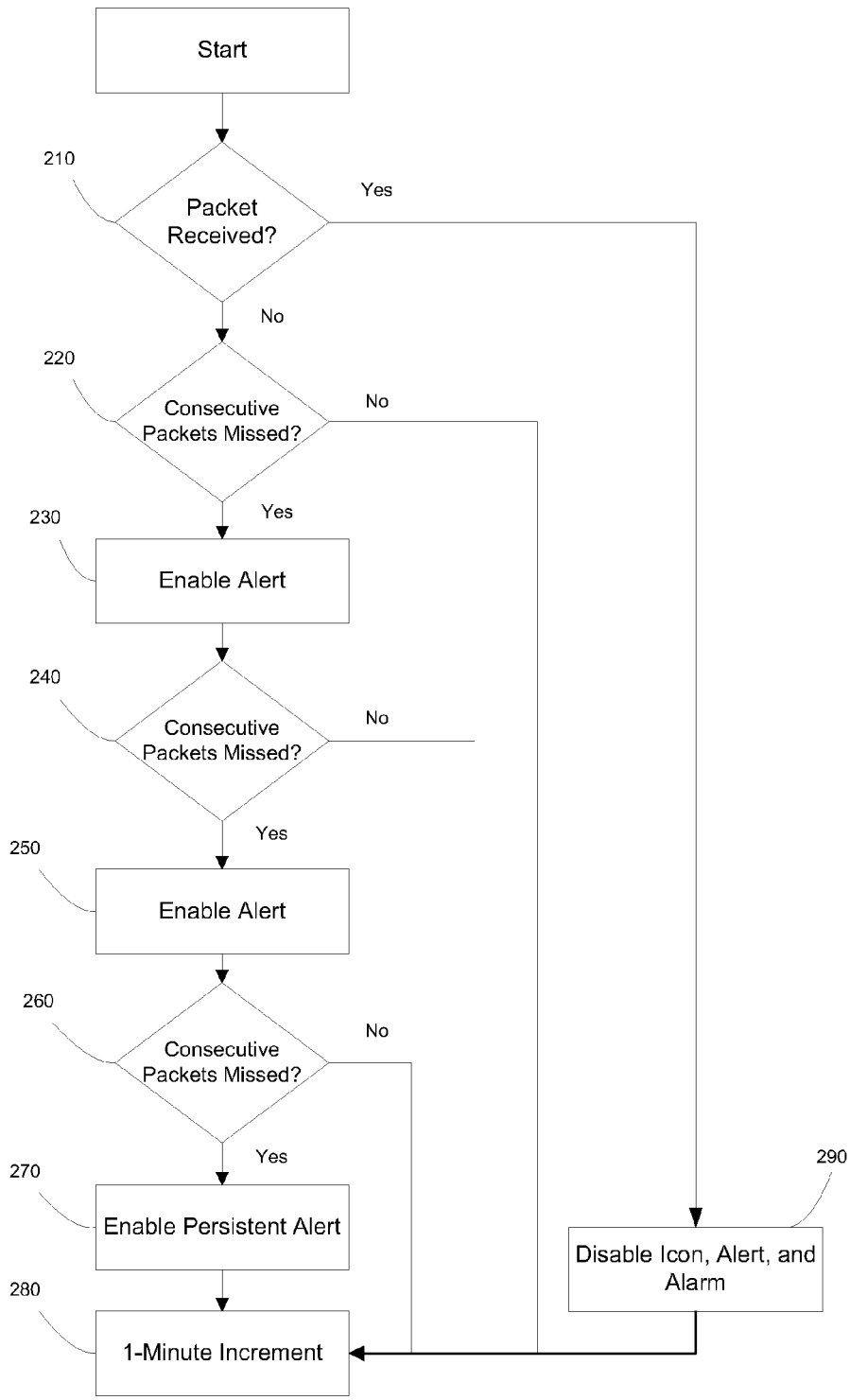
FIG. 2 is a flowchart illustrating a method for detecting a missed data packet and issuing an alert in accordance with one embodiment of the present disclosure.

FIG. 2 is a flowchart illustrating a method for detecting a missed data packet and issuing an alert in accordance with one embodiment of the present disclosure. As discussed above, a receiver, such as receiver 104 of the analyte monitoring system 100 of FIG. 1, may be configured to expect a data packet from a transmitter, such as transmitter 102 (FIG. 1) at regular time intervals. In certain embodiments, the time intervals may be every five minutes. In alternative embodiments, the time interval may be every minute. Still yet other embodiments provide that the interval may automatically change based on a detected condition of a user, a time of day, or a user initiated event, such as, for example, exercising, eating a meal, etc. Regardless of the time interval used, the receiver may be configured to anticipate a data packet at the selected or predetermined time interval.

Accordingly, in certain embodiments, as shown in FIG. 2, a processor of the receiver 104 is configured to determine whether data packets are received from the transmitter 102 at predetermined time intervals. In certain embodiments, the predetermined time intervals may be user selectable. In other embodiments, the predetermined time intervals are based on a monitored condition of a user. For example, if a rate of change of an analyte level of the user is within a predetermined threshold, the predetermined time interval may be three minutes. If the rate of change of the user's analyte level exceeds the threshold, the predetermined time interval may be one minute. If the processor determines that the receiver 104 has not received a data packet as expected (210) the receiver may be configured to attempt to recapture data packets automatically, requiring no user intervention. For example, the receiver 104 may issue a command to the transmitter 102 requesting that the transmitter 102 resend the last data packet. When the request is received, the transmitter 102 resends the last data packet via the communication link 103. If the processor detects that a single expected data packet was not received, the processor does not issue a command to generate an alert and the processor resumes detecting an arrival of a subsequent data packet.

If however, the processor detects that a first predetermined number (220) (e.g., two) of consecutive expected data packets were not received by the receiver 104, the processor issues a command to generate an alert notification (230). In certain embodiments, the alert notification may be a single alert or a series of alerts. Additionally, the alert notification may be an icon displayed on a display screen of the device, flashing lights, a warning screen and the like. Alternatively, the alert notification may be an auditory notification or a vibratory notification or a combination thereof.

In certain embodiments, the type of alert notifications may be user selectable. Additionally, the alerts may be color coded or have different volumes or vibration speeds based on a severity of the alert condition. For example, if the notification is a warning screen having text, the color of the text, a border of the screen or a background of text may be color coded based on number of consecutive data packets missed. In certain embodiments where the alert is an auditory alert, the tone and/or volume of the auditory alert may be user selectable. For example, if two data packets in a row were missed, two low volume beeps may sound. If however, three data packets in a row are missed, the volume may change to medium level and three beeps may sound. In embodiments, a user may select a tone, the length of the tone and the volume of the tone for each auditory notification. Finally, if the alert is a vibratory alert, the user may select the duration and/or frequency of the vibration.

Referring back to FIG. 2, once the alert is issued, the receiver 104 is configured to wait for a predetermined time interval, such as, for example, one minute, before checking the receipt of the next expected data packet. Although a one minute time interval is specifically mentioned, it is contemplated that the predetermined time interval may be more or less than one minute.

In certain embodiments, the predetermined time interval may automatically adjust based on the severity of the alert, such as, for example, the number of consecutive data packets not received. Thus, the higher the number of consecutive data packets not received, the smaller the predetermined time interval. Alternatively, the predetermined time interval may correspond to the interval at which the data packets are expected to arrive at the receiver 104. Thus, if data packets are expected to arrive at the receiver 104 every two minutes, the predetermined time interval is two minutes. Still yet other embodiments provide that the predetermined time interval corresponds to a fraction of time of the expected data packet arrival at the receiver 104. Thus, if a data packet is expected every five minutes, the predetermined time is two and a half minutes or some other fraction of time.

If the first predetermined number of consecutive data packets has not been received and there has been no user action to remedy the loss of the data packets, the processor of the receiver 104 detects whether a second predetermined amount of consecutive data packets has not been received. In certain embodiments, the count of consecutive data packets not received is not reset until at least one data packet is received. Other embodiments provide that the count of the number of consecutive data packets not received is reset by the processor after an alarm is acknowledged. If it is determined that a second predetermined number of consecutive data packets has not been received (240), the processor issues a command to generate a secondary alert (250) to notify the user to reconnect the receiver 104 and/or transmitter 102. For example, if five consecutive data packet are not received, an alert can be issued, by enabling an "RF MISSED A FEW" message or any other message or indication to indicate multiple data packets have been missed. As discussed above, the alert may be auditory, visual tactile or a combination thereof. If a user does not respond to the alert after a predetermined amount of time, the receiver 104 waits for a predetermined amount (280) of time before determining whether a subsequent data packet is received. In certain embodiments, because a second predetermined number of consecutive data packets were not received, the predetermined amount of time (280) may be reduced accordingly. For example, if five consecutive data packets were missed, the predetermined amount of time may be reduced from two minutes to one minute. Thus, as the number of consecutive data packets that are missed increases, the predetermined amount of time before checking the receipt of the next expected data packet is reduced.

If the processor of the receiver 104 detects a third predetermined number of consecutive expected data packets are not received by the receiver (260), the processor of the receiver 104 is configured to issue an alert (270), such as, for example, a persistent alarm that notifies the user to reconnect the receiver 104 to the transmitter 102. In certain embodiments, the persistent alert may not be mutable. Other embodiments provide that a user may silence or "snooze" the alert for a small amount of time. However, once the time period expires, the alert is triggered again. Other embodiments provide that if the alert is silenced repeatedly, the ability to silence the alarm is deactivated. Still yet other embodiments provide that the volume of the alert increase after each time the alert is snoozed or silenced. In certain embodiments, when the third predetermined number of consecutive alerts has been reached or exceeded, other alert notifications may be inactive. If the alert condition is not addressed by the user within a specified amount of time, the receiver 104 waits for the predetermined amount of time (280) before checking the receipt of the next expected data packet. If a data packet is not received, the alert is triggered.

In certain embodiments, regardless of how many consecutive data packets have been missed, the receiver 104 can be configured to de-assert (290) any issued alert after it successfully receives the next expected data packet subsequent to one or consecutive missed data packets. It will be recognized by one skilled in the art that the receiver can be configured to issue an alert and de-assert an alert based on a different number of consecutive missed data packets. For example, if five consecutive data packets have been missed and an alert has been issued, the receiver may be configured to de-assert the alert only when a predetermined number of consecutive data packets (e.g., three) have been received without interruption.

As discussed above, the alert issued by the receiver may contain one or more individual alarms. In one embodiment, the alert is a tri-modal alarm, which includes a visual notification (e.g., icon, message, or flashing lights), tactile notification (e.g., vibration) and audible (e.g., beep or ring tones, or music). Other sensory-stimulating alarm systems may be used including alerts which heat, cool, or produce a mild electrical shock when triggered.

In another aspect, the analyte monitoring system 100 (FIG. 1) includes an alarm notification feature to alert or warn a user of an event, such as, for example, a critical event like a potentially detrimental condition. For example, if glucose is the analyte, the alarm may notify a user of hypoglycemia, hyperglycemia, impending hypoglycemia, and/or impending hyperglycemia. In this regard, the alarm is configured such that when the data from the sensor 101 reaches or exceeds a threshold value, it outputs an alarm notification. Some non-limiting examples of threshold values for blood glucose levels are about 60, 70, or 80 mg/dL for hypoglycemia, about 70, 80, or 90 mg/dL for impending hypoglycemia, about 130, 150, 175, 200, 225, 250, or 275 mg/dL for impending hyperglycemia, and about 150, 175, 200, 225, 250, 275, or 300 mg/dL for hyperglycemia.

The threshold values that are designed into the alarm can correspond to interstitial fluid glucose concentrations or electrode measurements (e.g., current values or voltage values obtained by conversion of current measurements) that correlate to the above-mentioned blood glucose levels. The analyte monitor system may be configured so that the threshold levels for these or any other conditions may be programmable by the patient, caregiver or medical professional.

In certain embodiments, a threshold value is exceeded if a datapoint, such as a glucose datapoint, has a value that is above or below the threshold value indicating an impending or particular condition, such as hypoglycemia or hyperglycemia. For the purpose of illustration, a datapoint correlating to a glucose level of 200 mg/dL exceeds the threshold value (180 mg/dL) for hyperglycemia, and indicates that the monitored subject has already entered a hyperglycemic state. As another example, a datapoint correlating to a glucose level of 65 mg/dL exceeds a threshold value (70 mg/dL) for hypoglycemia and indicates that the monitored subject entered a hypoglycemic state. However, a datapoint correlating to a glucose level of 75 mg/dL would not exceed the same threshold value for hypoglycemia because the datapoint does not indicate a hypoglycemic state as defined by the predetermined threshold value.

The analyte monitoring system can also be configured to activate an alarm, such as by embedded software, if the sensor readings indicate that a value is beyond a measurement range of the sensor 101. For glucose, the physiologically relevant measurement range is typically about 50 to 250 mg/dL, preferably about 40 to 300 mg/dL and ideally 30 to 400 mg/dL, of glucose in the interstitial fluid. The alarm may also, or alternatively, be activated when the rate of change or acceleration of the rate of change in the analyte level increases or decreases at or above a predetermined threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

The alarm may be configured to output a notification if a single data point meets or exceeds a particular threshold value. Alternatively, the alarm may be configured to output a notification if a predetermined number of datapoints spanning a predetermined amount of time meet or exceed the threshold value. As another alternative, an alarm notification may be output only when the datapoints spanning a predetermined amount of time have an average value which meets or exceeds the threshold value. Each condition that can trigger an alarm may have a different alarm activation condition. In addition, the alarm activation condition may change depending on current conditions (e.g., an indication of impending hyperglycemia may alter the number of datapoints or the amount of time that is tested to determine hyperglycemia).

Figure 3:
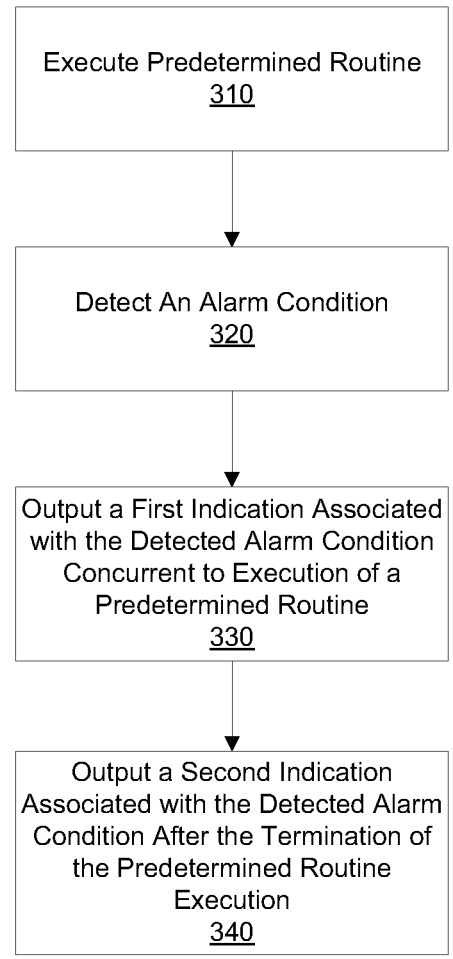
FIG. 3 is a flowchart illustrating a concurrent passive notification routine in a receiver of the analyte monitoring system in accordance with one embodiment of the present disclosure.

FIG. 3 is a flowchart illustrating a concurrent passive notification routine in a receiver of the analyte monitoring system according to one embodiment of the present disclosure. In certain embodiments, the analyte monitoring system, such as the analyte monitoring system 100 of FIG. 1, can include a concurrent passive notification routine. At the start of the concurrent passive notification routine, a processor of the receiver 104 (FIG. 1) executes a predetermined routine (310) for a time period until the routine is completed. Such routines may include blood glucose tests, calibration routines, medication dosage adjustments, such as a bolus dose or an update to a basal regiment. Other embodiments provide that the routine is a user initiated routine such as viewing various display screens on the receiver, updating system preferences, manually entering data such as, for example, event data, and the like. During the execution of the predetermined routine, an alarm condition is detected (320) by the processor of the receiver 104. In certain embodiments, the alarm condition may be triggered by a datapoint exceeding a threshold. When the alarm condition is detected, the processor causes a first indication associated with the detected alarm condition to be output concurrent with the execution of the predetermined routine (330).

In accordance with one embodiment, when the predetermined routine is being executed and an alarm condition is detected, a notification associated with the detected alarm condition is provided to the user without disrupting the routine. In certain embodiments, the alarm notification may be an audible beep or noise, a backlight indicator, an icon, a modification in any display item feature such as a border around a field that flashes, or a text output on the user interface display or any other suitable output indication to alert the user of the detected alarm condition substantially in real time, but which does not disrupt the ongoing routine. For example, when the predetermined routine is being executed, an icon or other visual indicator may be displayed in a corner of the current display screen of the predetermined routine to indicate that an alarm condition is detected.

Upon termination of the predetermined routine (340), another output or second indication associated with the detected alarm condition is output or displayed. In certain embodiments, the processor of the receiver 104 may detect that the predetermined routine has terminated and subsequently output the second indication. For example, if the predetermined routine is a calibration routine, the processor detects when the calibration is complete. In other embodiments, such as, for example, user initiated routines, the termination of the routine may be determined or detected based on a user activated event via the user interface. In certain embodiments, the second indication associated with the detected alarm condition is sounded and/or displayed more prominently. For example, and as described above, as the predetermined routine is executing, the alarm may be a soft tone or sound, a discretely displayed icon or textual message, a slight color change to the background of the current display screen and the like. However, when the routine is finished executing, the alarm is sounded or displayed prominently to indicate the detection of the alert condition.

In a further aspect, the user interface notification feature associated with the detected alarm condition is output to the user only upon the completion of an ongoing routine which was in the process of being executed when the alarm condition was detected.

In another aspect, the receiver is configured to provide a user the capability to disenable the alarm notification output for a predetermined time period and to re-enable the alarm notification prior to termination of the predetermined time period. Thus, if the user is running a routine or a series of routines that will take a substantial amount of time, the user may select to disenable the output of the first alarm and/or the output of the second alarm for a predetermined amount of time. In one embodiment, a glucose monitoring system is configured to allow the user to disenable an alarm notification, via a user interface, only if the user's blood glucose level is within predetermined parameters, such as for example, between about 60 and 139 mg/dL.

As discussed above, the alarm may contain one or more individual alarms. In one embodiment, the alarm is a tri-modal alarm, which includes a visual notification (e.g., icon or flashing lights), tactile notification (e.g. vibration) and audible (e.g., beep or ring tones, or music). Other sensory-stimulating alarm systems may be used including alarms which heat, cool, or produce a mild electrical shock when triggered. In some embodiments, auditory alarms have different tone, note, or volume indicating different conditions. For example, a high note might indicate hyperglycemia and a low note might indicate hypoglycemia. Visual alarms may use a difference in color, brightness to indicate different conditions or severity levels. In some embodiments, an auditory alarm is configured so that the volume of the alarm increases over time until the alarm is deactivated.

In some embodiments, the alarm may be automatically deactivated after a predetermined time period. In other embodiments, the alarm may be configured to deactivate when the data no longer indicates that the condition which triggered the alarm exists. In these embodiments, the alarm may be deactivated when a single data point indicates that the condition no longer exists or, alternatively, the alarm may be deactivated only after a predetermined number of datapoints or an average of the datapoints obtained over a given period of time indicate that the condition no longer exists.

Other embodiments provide that the alarm may be deactivated manually by a user. In these embodiments, a switch is provided and when actuated, the alarm is turned off. The switch may be operatively engaged (or disengaged depending on the configuration of the switch) by, for example, operating an actuator on sensor 101 or the receiver/display unit 104. In some cases, an actuator may be provided on two or more units including the sensor 101, transmitter 102, primary receiver 104, secondary receiver 106, or elsewhere, any of which may be actuated to deactivate the alarm.

A variety of switches may be used including, for example, a mechanical switch, a reed switch, a Hall effect switch, a Gigantic Magnetic Ratio (GMR) switch (the resistance of the GMR switch is magnetic field dependent) and the like. Preferably, the actuator used to operatively engage (or disengage) the switch is placed on the sensor 101 and configured so that no water can flow around the button and into the housing. One example of such a button is a flexible conducting strip that is completely covered by a flexible polymeric or plastic coating integral to the housing. In an open position the flexible conducting strip is bowed and bulges away from the housing. When depressed by the patient or another person, the flexible conducting strip is pushed directly toward a metal contact and completes the circuit to shut off the alarm.

In instances when a reed or GMR switch is used, a flexible actuator containing a magnetic material, such as a permanent magnet or an electromagnet may be used to deactivate the alarm. In such embodiments, the flexible actuator may bulge away from the housing. Thus, when reed or GMR switch is activated (to deactivate the alarm) by depressing the flexible actuator, the magnetic material is brought closer to the switch which causes an increase in the magnetic field within the switch and the alarm is deactivated.

Figure 4:
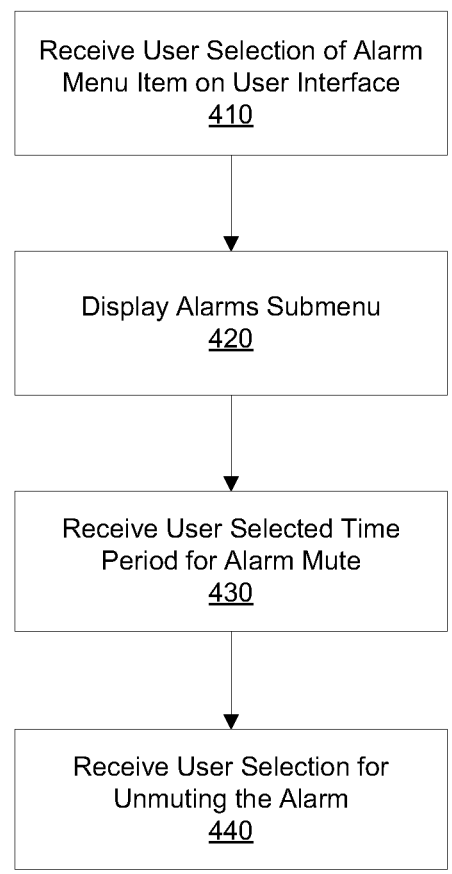
FIG. 4 is a flowchart illustrating an alarm notification disenabling and re-enabling routine in a receiver of the analyte monitoring system in accordance with one embodiment of the present disclosure.

FIG. 4 is a flowchart illustrating an alarm notification disenabling and re-enabling routine in a receiver of the analyte monitoring system in accordance with one embodiment of the present disclosure. In certain embodiments and as described below, the analyte monitoring system 100 (FIG. 1) provides a user with the capability to disenable the alarm prior to activation of an alarm notification by a particular event, such as a single data point exceeding a threshold, a hyperglycemic state, a decreasing trend of analyte concentrations. In this regard, a user can access the alarms menu to disenable and re-enable the alarm from a user interface of analyte monitoring system.

The routine for disenabling and re-enabling alarm notifications begins when a user is presented with a user interface on a receiver 104 (FIG. 1) and the user makes a selection of one of the options thereon (410). In certain embodiments, the user interface includes a main menu having a plurality of selection options. Nonlimiting examples of the selection options may include "Glucose," "Alarms," "Reports," "System," and "Add Event." A user may navigate the list of options and select one of the options using an actuator disposed on the receiver 104, such as, for example, a jog wheel, arrow keys on the receiver, a touch sensitive portion of the display and the like. When a processor of the receiver 104 detects user selection of the "Alarms" option, a submenu for the "Alarms" option is displayed (420). In certain embodiments, the submenu of the "Alarms" option that includes an alarm menu for disenabling and/or muting alarms is displayed only if the alarm notification is not already disenabled (for example audible alarm muted). Alternatively, the submenu user interface that includes an alarm menu for disenabling and/or muting alarms is displayed regardless of whether alarm notifications are disenabled. Still yet other embodiments provide that selection of the submenu will only display alarms that can be muted or disenabled.

When the mute alarm option is selected from user menu the receiver displays a user interface that allows a user to select a predetermined period of time for disenablement or muting of the alarm notification (430). In embodiments, user selection is enabled using an actuator disposed on the receiver 104. Selectable predetermined periods can be twelve or less hours. Further, the predetermined time for more than one hour can be by hourly increments. In still yet further embodiments, when a user desires to re-enable the alarm notification, the user interface of the receiver 104 provides a display screen with the option to re-enable the alarm notification feature. In this regard, the user interface provides a menu selection to enable the user to un-mute the alarm notification (440). In certain embodiments, the user interface for alarm re-enablement only shows alarms which have been previously disenabled and/or muted.

If desired, the display screen of receiver 104 is configured to blank the user interface if no selection is made in a predetermined period of time. For example, the receiver 104 can be configured to blank or fade to black within twenty or more seconds if no selection is made. Other embodiments provide that if a user selection is not made in a predetermined time period, the user is returned to the main menu screen.

In one embodiment, an icon is displayed on the receiver display to indicate alarms are disenabled and/or muted. In some embodiments, the user is allowed to turn off low and high glucose alarms only if the user turns off each alarm mode individually.

Figure 5:
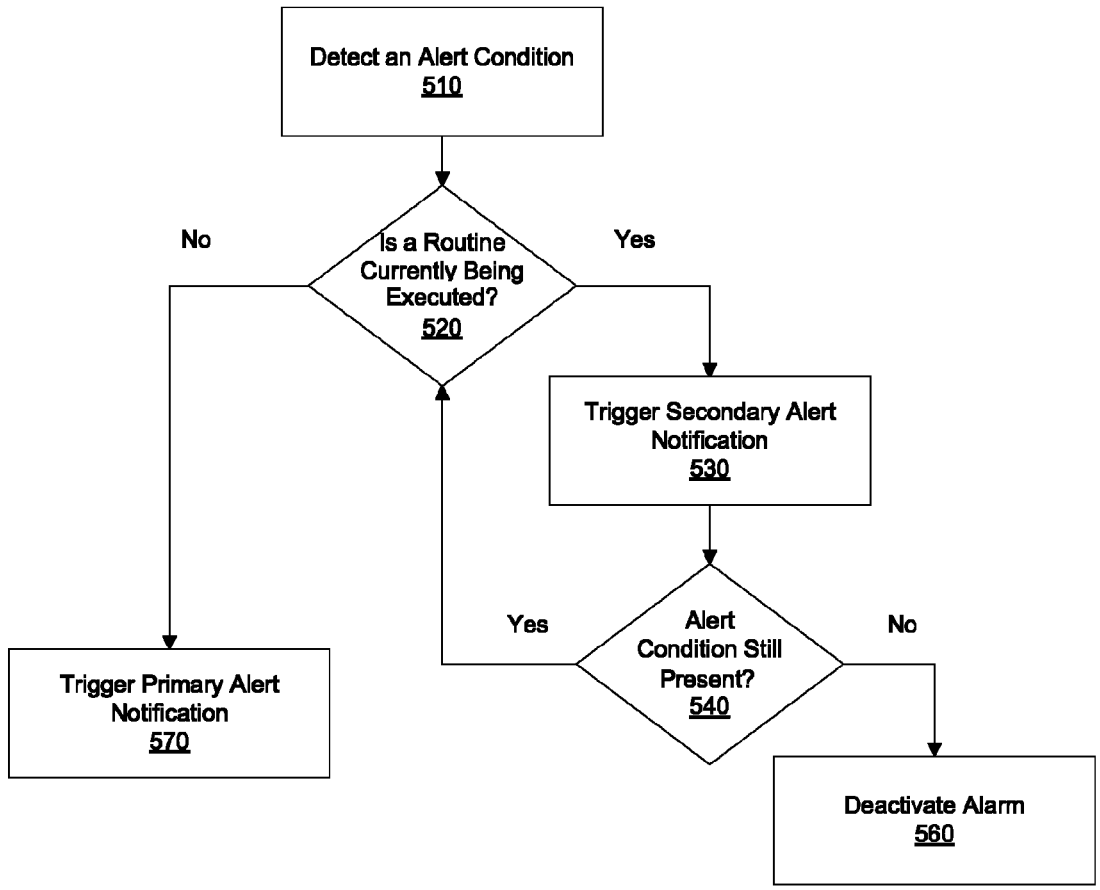
FIG. 5 is a flowchart illustrating a method for detecting an alert condition in accordance with one embodiment of the present disclosure.

FIG. 5 is a flowchart illustrating a method for detecting an alert condition in accordance with one embodiment of the present disclosure. At the start of the routine, a processor of the receiver 104 (FIG. 1) detects an alert condition (510). In embodiments, the alert condition may be detected because of a critical event such as a low glucose level of a user, a decreasing blood glucose trend of the user, a hypoglycemic event, or a blood glucose level above or below a particular threshold level. In other embodiments, the detected alert condition may correspond to non-critical such as, for example, low battery status or low sensor life.

When an alert condition is detected, the processor determines whether a routine is currently being executed (520). Such routines may include blood glucose tests, calibration routines, and medication dosage adjustments, such as a bolus dose or an update to a basal regiment. Other embodiments provide that the routine is a user initiated routine such as viewing various display screens on the receiver 104, updating system preferences, or manually entering data into the receiver.

If the processor determines that a routine is not currently being executed, such as, for example, by detecting an idle state of the receiver, the processor issues a command to generate a primary alert notification (570). In one embodiment, the alert notification may include a visual notification (e.g., icon, message, or flashing lights), a tactile notification (e.g. vibration), an audible notification (e.g., beep or ring tones, or music) or a combination thereof.

If the processor determines that a routine is currently being executed, the processor of the receiver 104 issues a command to generate a secondary alert notification (530). In embodiments, the secondary alert notification is displayed or otherwise activated so as to not disrupt the routine that is currently being executed. Thus, in certain embodiments, the alarm notification may be an audible beep or noise, a backlight indicator, an icon, a modification in any display item feature such as a border around a field that flashes, or a text output on the user interface display that may be output substantially simultaneously with the routine.

After the secondary alert is generated by the processor, the processor determines whether the condition that triggered the alarm is still present (540). For example, if a low battery triggered the alert condition, the processor determines whether the battery has been recharged or is currently recharging. If the alert condition was triggered because a blood glucose level was above or below a particular threshold, the processor determines whether a recent blood glucose level reading is within the predetermined threshold. If it is determined that the condition that triggered the alert no longer exists, the processor issues a command to deactivate the alarm (560).

If however, it is determined that the condition that triggered the alert still exists, the processor once again determines whether the routine is currently being executed (520). If it is determined that the routine is no longer being executed, the processor issues a command to trigger the primary alert notification (570) as described above. However, if it is determined that the routine is no longer being executed and the condition that triggered the alert no longer exists, the processor issues a command to deactivate any alarms that may still be active.

The various embodiments of detecting missed data packets, issuing alerts, and disenabling and enabling the alerts can be implemented in the receiver which comprises a processor, and a computer readable medium for storing data relating to the operation of the analyte monitoring device and software, which when executed by the processor, determines whether a data packet from the transmitter is not received, or otherwise missed by the receiver, and whether to issue an alert to the user. Thus, the receiver is configured to expect a data packet and issue an alert when an expected data packet is not received.

In one embodiment, an analyte monitoring system includes a sensor in operative contact with an analyte, the sensor adapted to generate a data signal associated with an amount or concentration of the analyte; a transmitter operatively coupled to the sensor and adapted to process the raw data signal generated by the sensor to define a data packet, wherein the data packet comprises a current analyte value and the previous two analyte values; and a receiver operatively linked to the transmitter and capable of receiving the data packet from the transmitter, wherein the receiver is configured to alert a user if at least two consecutive data packets are not received by the receiver.

In another embodiment, the receiver receives the data packet from the transmitter via a radio-frequency communications link.

Further embodiments provide that the alert is a visual alert such as, for example, an icon.

In an embodiment, the alert is an audible alert such as a beep, a tone or music.

In still yet other embodiments, the alert is a tactile alert such as, for example, a vibration of a component of the analyte monitoring system.

Embodiments also include configurations where the receiver alerts the user to reconnect the receiver or the transmitter if more than two consecutive data packets are not received by the receiver.

In certain embodiments, the receiver is configured to expect a data packet from the transmitter every five minutes or less or every minute or less.

In one aspect, the alert automatically disengages when a data packet is received by the receiver subsequent to non-receipt of an earlier data packet.

In another aspect, the alert is a continuous alert if the receiver fails to receive more than five consecutive data packets from the transmitter.

In certain embodiments, the analyte is glucose, and the analyte monitoring system is a continuous glucose monitoring system.

Still yet other embodiments provide that the receiver is wirelessly linked to a data management host.

In other embodiments, the sensor comprises a substrate, a working electrode, a counter electrode, and a reference electrode arranged in a stacked orientation, and further wherein each of the electrodes is formed from a conductive material.

In another embodiment an analyte monitoring system includes a sensor in operative contact with an analyte, the sensor adapted to generate a data signal associated with an amount or concentration of the analyte; a transmitter coupled to the sensor and adapted to process the data signal generated by the sensor; and a receiver capable of receiving the processed data signal and outputting an alarm notification based on an event, wherein the receiver is configured to allow a user to disenable the alarm notification for a predetermined time period and to re-enable the alarm notification prior to elapse of the predetermined time period.

In one embodiment, the alarm is a tri-modal alarm and includes an audible alarm, a visual alarm and a tactile alarm.

In yet another embodiment, the receiver is adapted to disenable only one mode of the alarm.

In one aspect, the disenabled alarm notification is muting an audible alarm.

In another aspect, the predetermined time is about one to twelve hours.

In yet another aspect, the predetermined period is more than one hour and further the mute is set in one hour increments for the entire predetermined period.

Embodiments provide that the receiver is capable of displaying an icon indicator when the alarm is muted.

Other embodiments provide that the alarm is incapable of being disenabled by a user for a critical event such as, for example, a low glucose event.

In one embodiment, the event is a system or data loss event.

Still yet other embodiments provide that the sensor further includes insulating material disposed between the electrodes.

Embodiments also provide that a sensing layer is disposed on at least a portion of at least the working electrode, the sensing layer including at least one immobilized enzyme and an immobilized mediator agent.

In certain embodiments, the sensor further includes a biocompatible membrane disposed on at least a portion of the sensing layer.

Embodiments provide that the biocompatible membrane is at least partially bonded to the sensing layer to define a heterogeneous multilayer.

In an embodiment, the transmitter is worn on the body of a user.

In an embodiment, the transmitter is a temperature sensor.

Embodiments also provide that the receiver has a memory capable logging analyte concentration or amount values.

Still further embodiments provide that the receiver is configured to allow a user to erase the logged analyte concentration or amount values.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. An analyte monitoring system, comprising:
   an analyte sensor in fluid contact with interstitial fluid, the analyte sensor adapted to generate a signal associated with an analyte level;
   a sensor electronics operatively coupled to the analyte sensor and adapted to generate a data packet, wherein the data packet corresponds to a current analyte value and a plurality of prior analyte values; and
   a data receiver in signal communication with the sensor electronics and configured to receive the data packet from the sensor electronics, the data receiver further configured to automatically output a first alert notification when a first predetermined number of data packets is not received by the data receiver, and automatically output a second alert notification when a second predetermined number of data packets is not received by the data receiver.

2. The analyte monitoring system of claim 1, wherein the second alert notification is different than the first alert notification.

3. The analyte monitoring system of claim 1, wherein each of the first alert notification and the second alert notification is one of an auditory notification, a tactile notification or a visual notification.

4. The analyte monitoring system of claim 1, wherein the data receiver is configured to automatically output the first alert notification when a first predetermined number of consecutive data packets is not received by the data receiver, and automatically output the second alert notification when a second predetermined number of consecutive data packets is not received by the data receiver.

5. A method, comprising:
   detecting when a first predetermined number of data packets is not received;
   outputting a first alert notification type when the first predetermined number of data packets is not received;
   detecting when a second predetermined number of data packets is not received; and
   outputting a second alert notification type when the second predetermined number of data packets is not received, wherein the first alert notification type is output at a first predetermined output level and wherein the second alert notification type is output at a second predetermined output level.

6. The method of claim 5, further comprising expecting an arrival of a subsequent data packet at a first predetermined period of time when the first predetermined number of data packets is not received.

7. The method of claim 6, wherein the first predetermined period of time is based, at least in part, on the first predetermined number of data packets that were not received.

8. The method of claim 5, further comprising expecting an arrival of a subsequent data packet at a second predetermined period of time when the second predetermined number of data packets is not received.

9. The method of claim 8, wherein the second predetermined period of time is based, at least in part, on the second predetermined number of data packets that were not received.

10. The method of claim 5, wherein the first alert notification type is disenabled when a subsequent data packet is received.

11. The method of claim 5, wherein the first alert notification type is disenabled when a predetermined number of subsequent data packets are received.

12. The method of claim 5, wherein the second alert notification type is disenabled when a subsequent data packet is received.

13. The method of claim 5, wherein the second alert notification type is disenabled when a predetermined number of subsequent data packets are received.

14. The method of claim 5, further comprising selectively dis-enabling at least one of the first alert notification type or the second alert notification type.

15. The method of claim 5, wherein the first alert notification type is output when a first predetermined number of consecutive data packets is not received, and further, wherein the second alert notification type is output when a second predetermined number of consecutive data packets is not received.

16. A method, comprising:
   detecting an occurrence of a predetermined routine;
   detecting an occurrence of an alarm condition when a first predetermined number of data packets is not received;
   outputting a first notification of the alarm condition at a first output level;
   detecting a termination of the predetermined routine; and outputting a second notification of the alarm condition at a second output level when the predetermined routine is terminated.

17. The method of claim 16, wherein the first notification of the alarm condition is output concurrently with the occurrence of the predetermined routine.

18. The method of claim 16, further comprising disenabling at least one of the first notification and the second notification.

19. The method of claim 16, wherein the predetermined routine is one of a blood glucose test, a calibration routine, or a medication dosage adjustment.

20. The method of claim 16, wherein detecting the occurrence of the alarm condition includes detecting the alarm condition when a first predetermined number of consecutive data packets is not received.

* * * * *